United States Patent
Sato et al.

(10) Patent No.: US 10,551,721 B2
(45) Date of Patent: Feb. 4, 2020

(54) RADIATION IMAGING APPARATUS, CONTROL METHOD THEREOF AND RADIATION IMAGING SYSTEM

(71) Applicant: CANON KABUSHIKI KAISHA, Tokyo (JP)

(72) Inventors: Eriko Sato, Tokyo (JP); Toshio Kameshima, Kawasaki (JP); Tomoyuki Yagi, Chofu (JP); Hideyuki Okada, Honjo (JP); Takuya Ryu, Kokubunji (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 15/561,122

(22) PCT Filed: May 27, 2016

(86) PCT No.: PCT/JP2016/002573
§ 371 (c)(1),
(2) Date: Sep. 25, 2017

(87) PCT Pub. No.: WO2017/002301
PCT Pub. Date: Jan. 5, 2017

(65) Prior Publication Data
US 2018/0129120 A1 May 10, 2018

(30) Foreign Application Priority Data

Jul. 2, 2015 (JP) .................................. 2015-133921

(51) Int. Cl.
*G03B 7/08* (2014.01)
*G03B 42/02* (2006.01)
(Continued)

(52) U.S. Cl.
CPC ............... *G03B 7/08* (2013.01); *A61B 6/542* (2013.01); *G01T 1/17* (2013.01); *G03B 42/02* (2013.01); *H04N 5/32* (2013.01)

(58) Field of Classification Search
CPC .......... G03B 7/08; G03B 42/02; A61B 6/542; G01T 1/17; H04N 5/32
See application file for complete search history.

(56) References Cited

U.S. PATENT DOCUMENTS

| | | | | |
|---|---|---|---|---|
| 6,330,303 B1 * | 12/2001 | Yamane | ................. | A61B 6/032 250/370.09 |
| 7,227,926 B2 | 6/2007 | Kameshima et al. | ....... | 378/98.9 |

(Continued)

FOREIGN PATENT DOCUMENTS

| | | |
|---|---|---|
| CN | 102525519 | 7/2012 |
| CN | 102648852 | 8/2012 |

(Continued)

*Primary Examiner* — Christine S. Kim
(74) *Attorney, Agent, or Firm* — Venable LLP

(57) ABSTRACT

A radiation imaging apparatus that includes a plurality of sensors, a readout unit and a control unit, wherein the control unit performs a first control of reading out signals from sensors after radiation irradiation is started, and a second control of outputting a control signal to end the radiation irradiation when a calculated value calculated based on an output of the readout unit in the first control reaches a reference value, and the control unit, in the first control, reads out the signals from the sensors by changing a signal amplification ratio of the readout unit such that a value of an output of the readout unit is not saturated, and, in the second control, calculates the calculated value by accumulating the output of the readout unit in consideration of the signal amplification ratio.

23 Claims, 7 Drawing Sheets

(51) Int. Cl.
*A61B 6/00* (2006.01)
*G01T 1/17* (2006.01)
*H04N 5/32* (2006.01)

(56) References Cited

U.S. PATENT DOCUMENTS

| | | | |
|---|---|---|---|
| 7,381,963 B2 | 6/2008 | Endo et al. | 250/370.09 |
| 7,408,167 B2 | 8/2008 | Kameshima et al. | 250/370.09 |
| 7,476,027 B2 | 1/2009 | Takenaka et al. | 378/207 |
| 7,514,663 B2 | 4/2009 | Yagi et al. | 250/208.1 |
| 7,532,706 B2 | 5/2009 | Kameshima et al. | 378/98 |
| 7,732,778 B2 | 6/2010 | Yokoyama et al. | 250/370.08 |
| 7,839,977 B2 | 11/2010 | Kameshima et al. | 378/116 |
| 8,072,514 B2 | 12/2011 | Takenaka et al. | 348/246 |
| 8,604,434 B2 | 12/2013 | Kobayashi | |
| 8,723,996 B2 | 5/2014 | Yokoyama et al. | H04N 5/335 |
| 8,829,438 B2 | 9/2014 | Sato et al. | G01J 1/00 |
| 9,423,512 B2 | 8/2016 | Sato et al. | G01T 1/17 |
| 9,445,030 B2 | 9/2016 | Yagi et al. | H04N 5/378 |
| 9,470,800 B2 | 10/2016 | Iwashita et al. | G01T 1/16 |
| 9,470,802 B2 | 10/2016 | Okada et al. | G01T 1/208 |
| 9,541,653 B2 | 1/2017 | Iwashita et al. | G01T 1/17 |
| 9,655,586 B2 | 5/2017 | Yagi et al. | A61B 6/585 |
| 9,737,271 B2 | 8/2017 | Iwashita et al. | A61B 6/4208 |
| 9,812,474 B2 | 11/2017 | Yagi et al. | H01L 27/14609 |
| 2011/0317054 A1 | 12/2011 | Kameshima et al. | 348/302 |
| 2012/0140886 A1 | 6/2012 | Murakoshi et al. | |
| 2013/0136234 A1 | 5/2013 | Noma et al. | 378/91 |
| 2013/0223592 A1 | 8/2013 | Sato | |
| 2014/0061488 A1 | 3/2014 | Sato et al. | 250/370.08 |
| 2014/0239186 A1 | 8/2014 | Sato et al. | G01T 1/17 |
| 2016/0377737 A1 | 12/2016 | Okada et al. | G01T 1/17 |
| 2017/0285189 A1 | 10/2017 | Ryu et al. | G01T 1/247 |

FOREIGN PATENT DOCUMENTS

| | | |
|---|---|---|
| CN | 103284736 | 9/2013 |
| JP | 2010-075556 | 4/2010 |
| JP | 2013-098796 | 5/2013 |

\* cited by examiner

[Fig. 1]
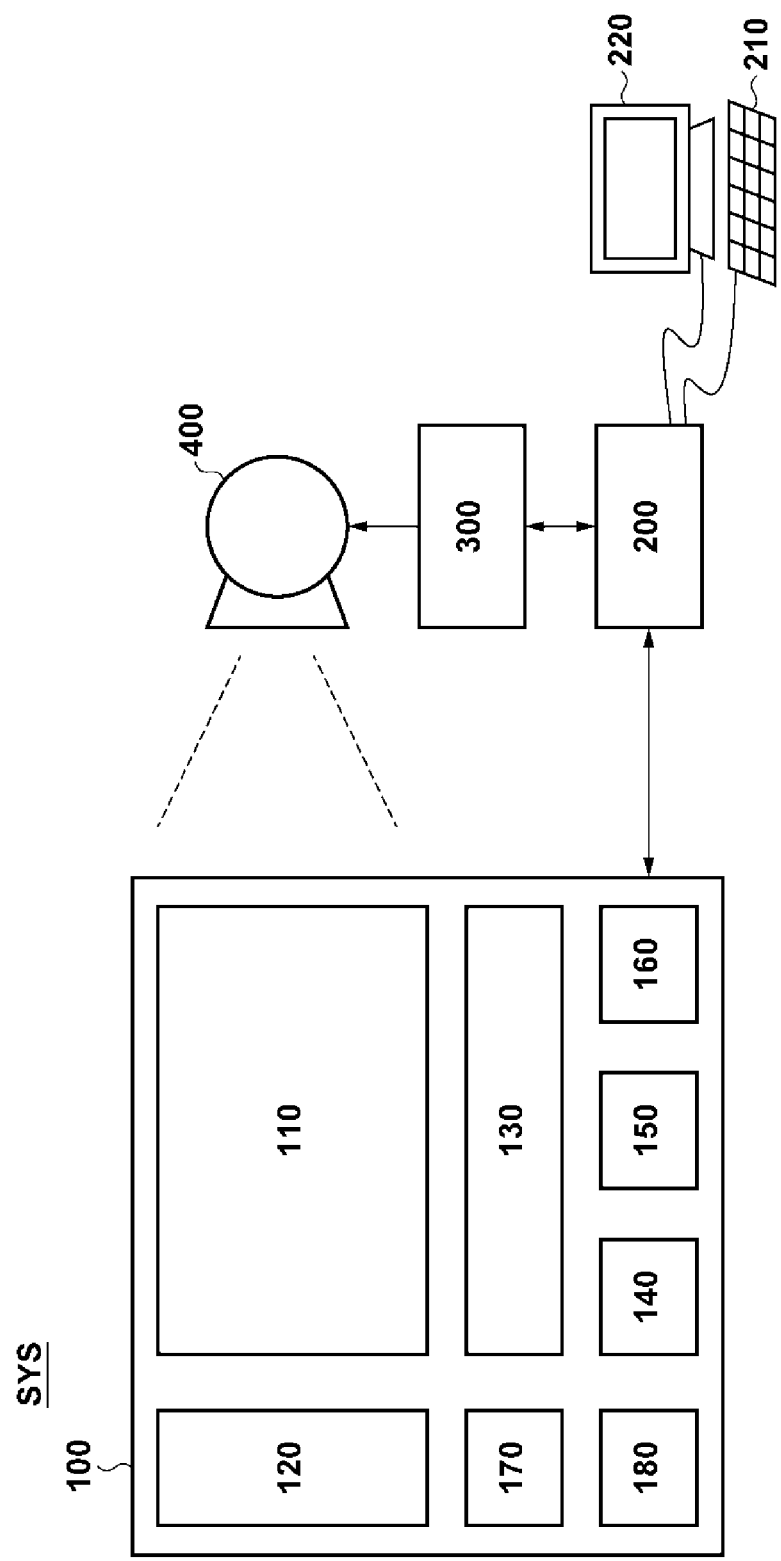

[Fig. 2]
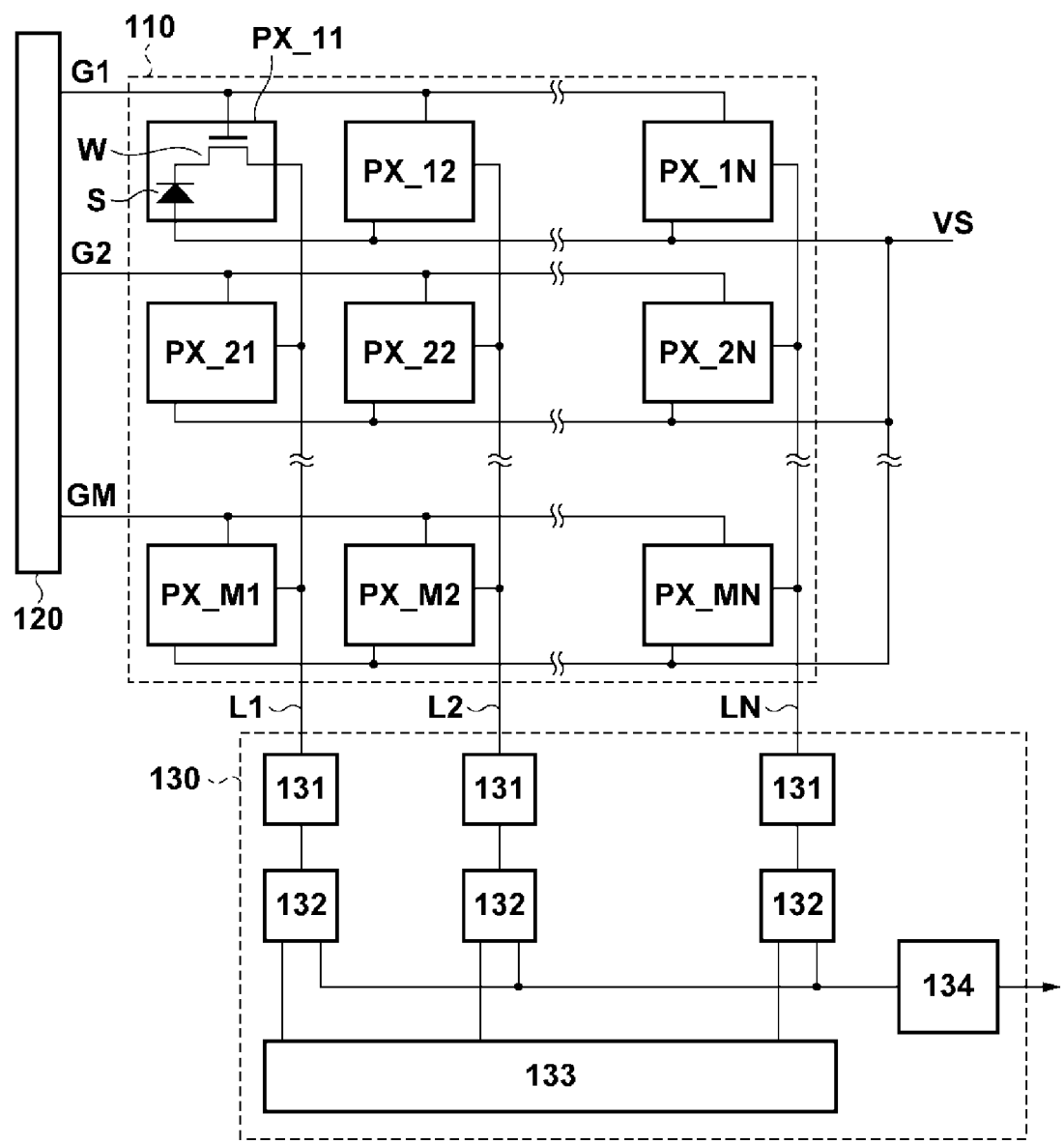

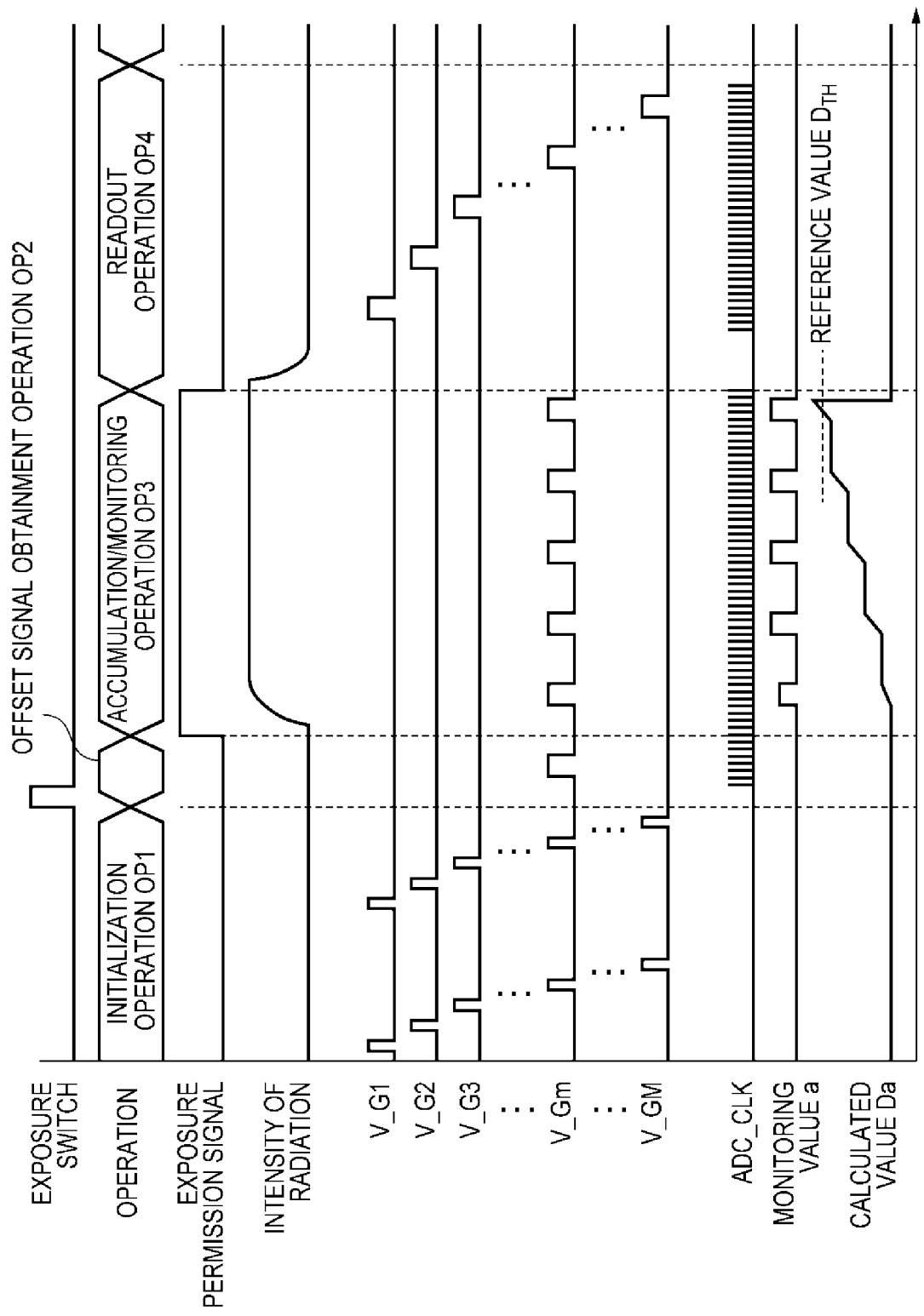
[Fig. 3]

[Fig. 4]
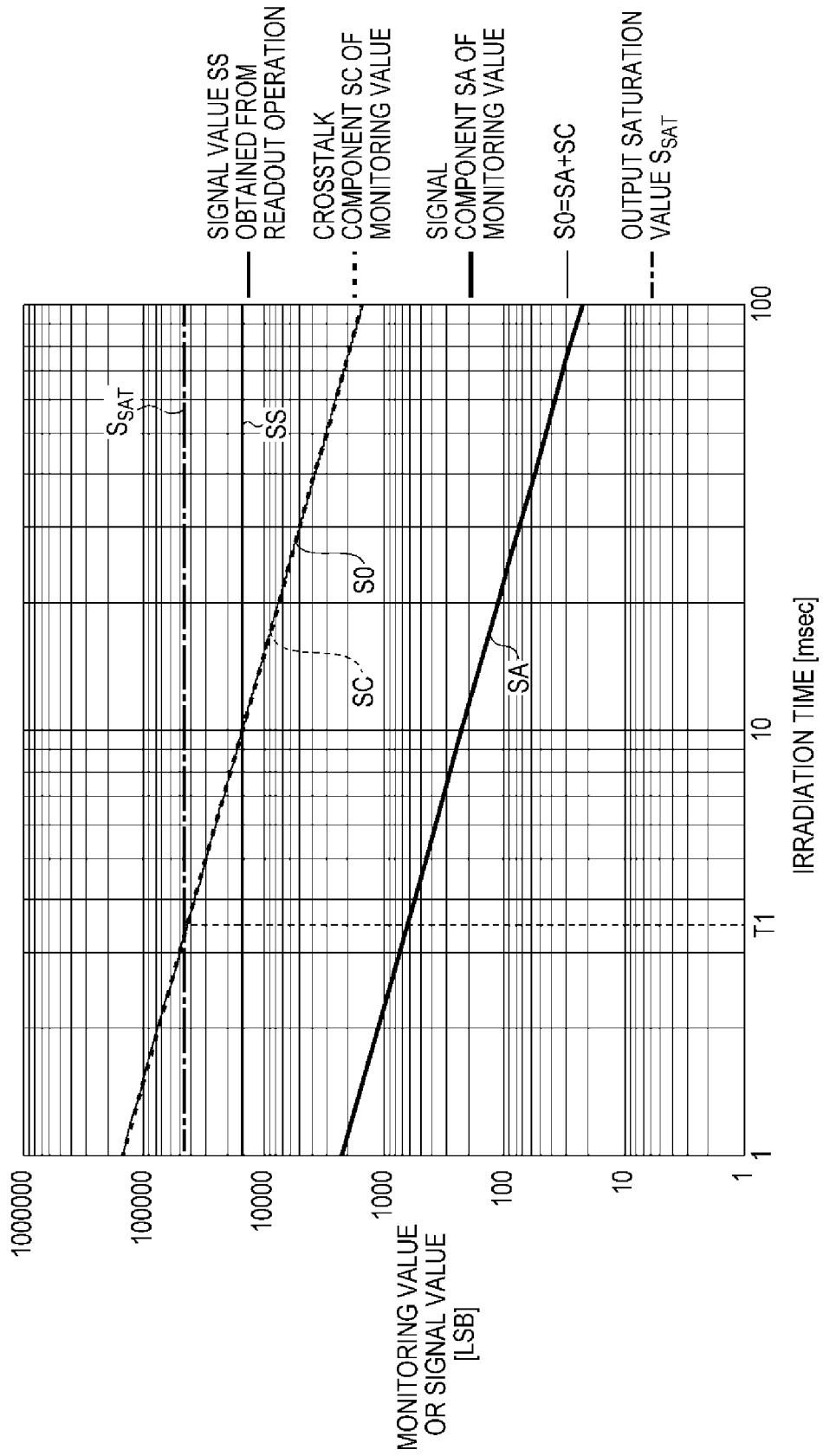

[Fig. 5]
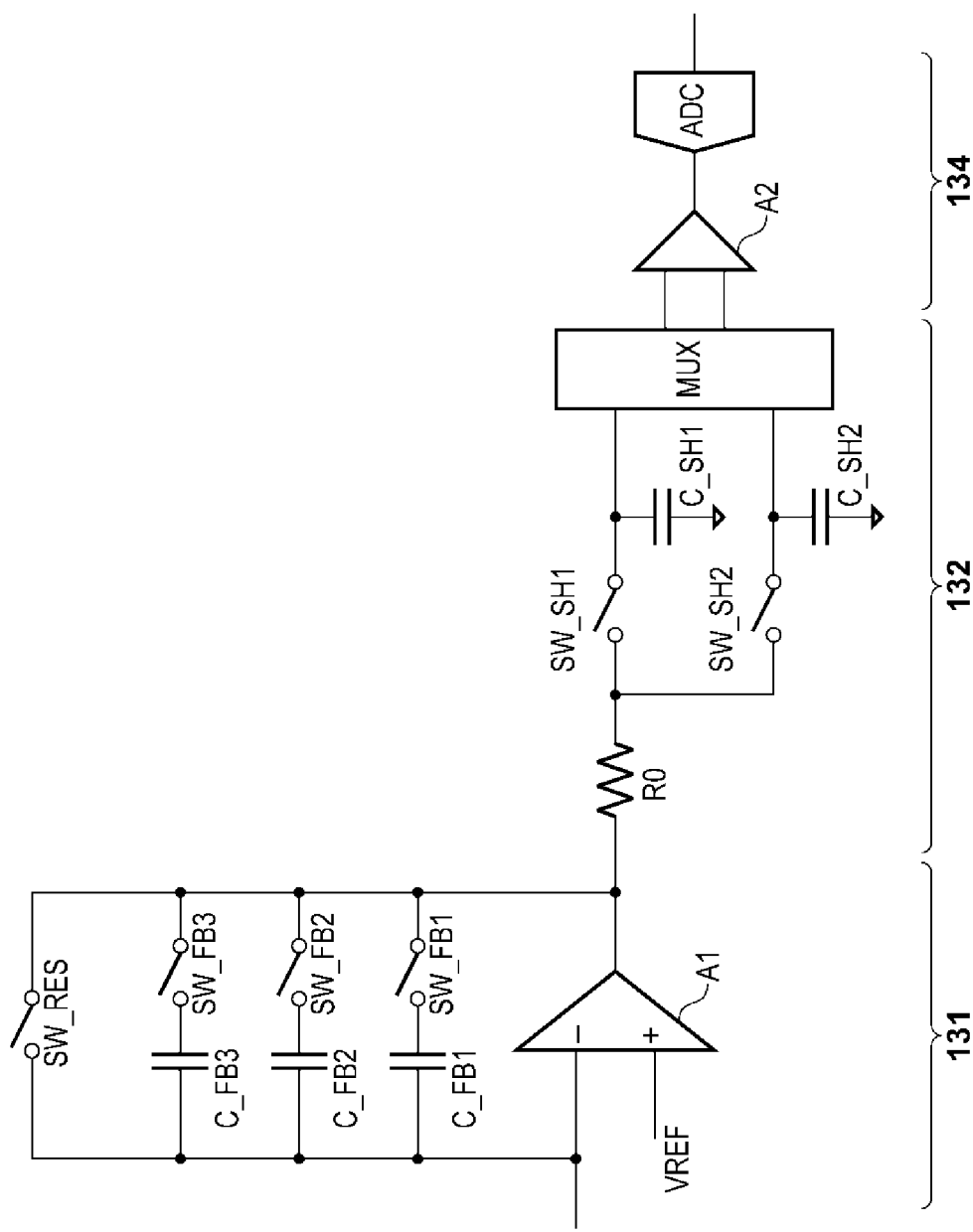

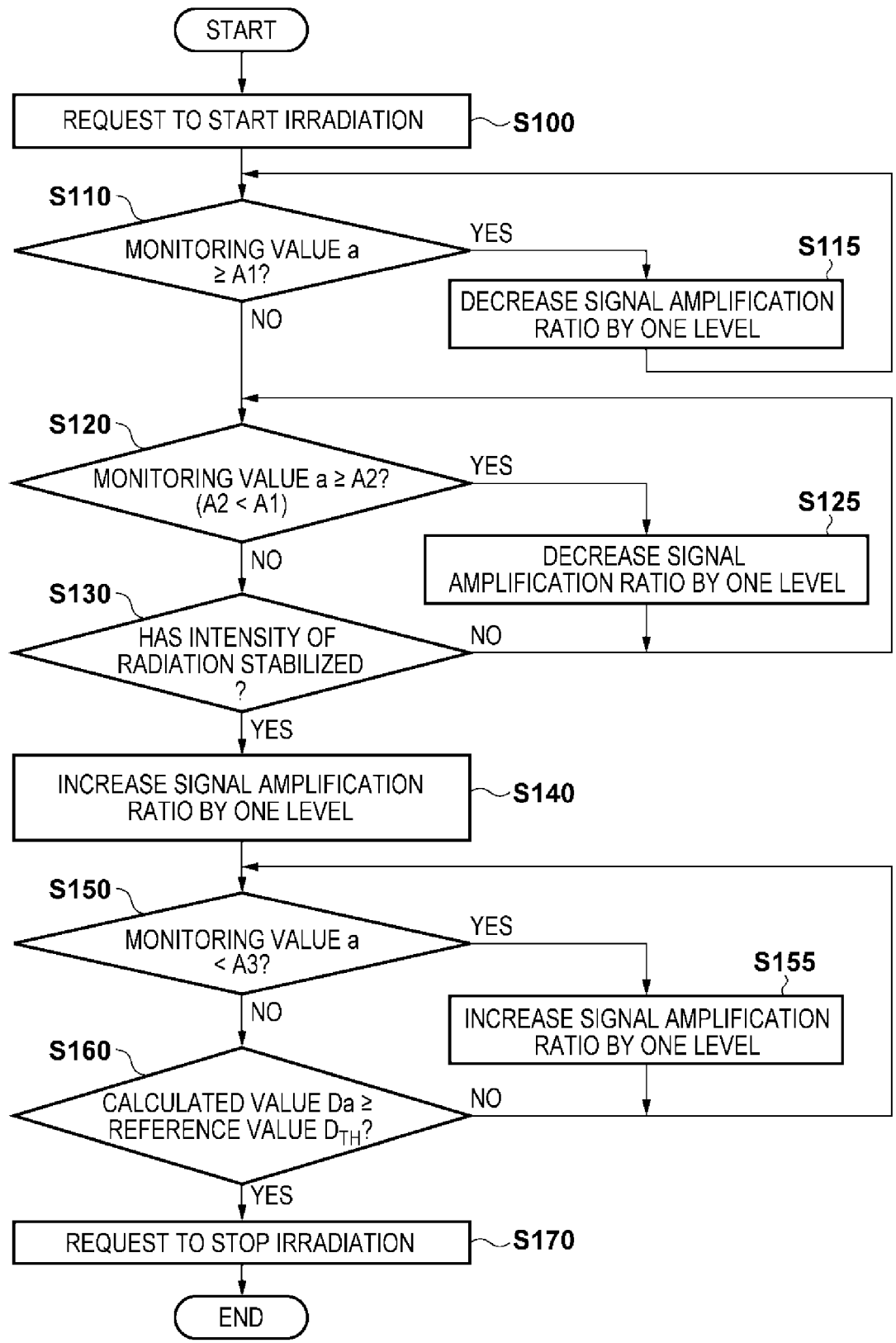
[Fig. 6]

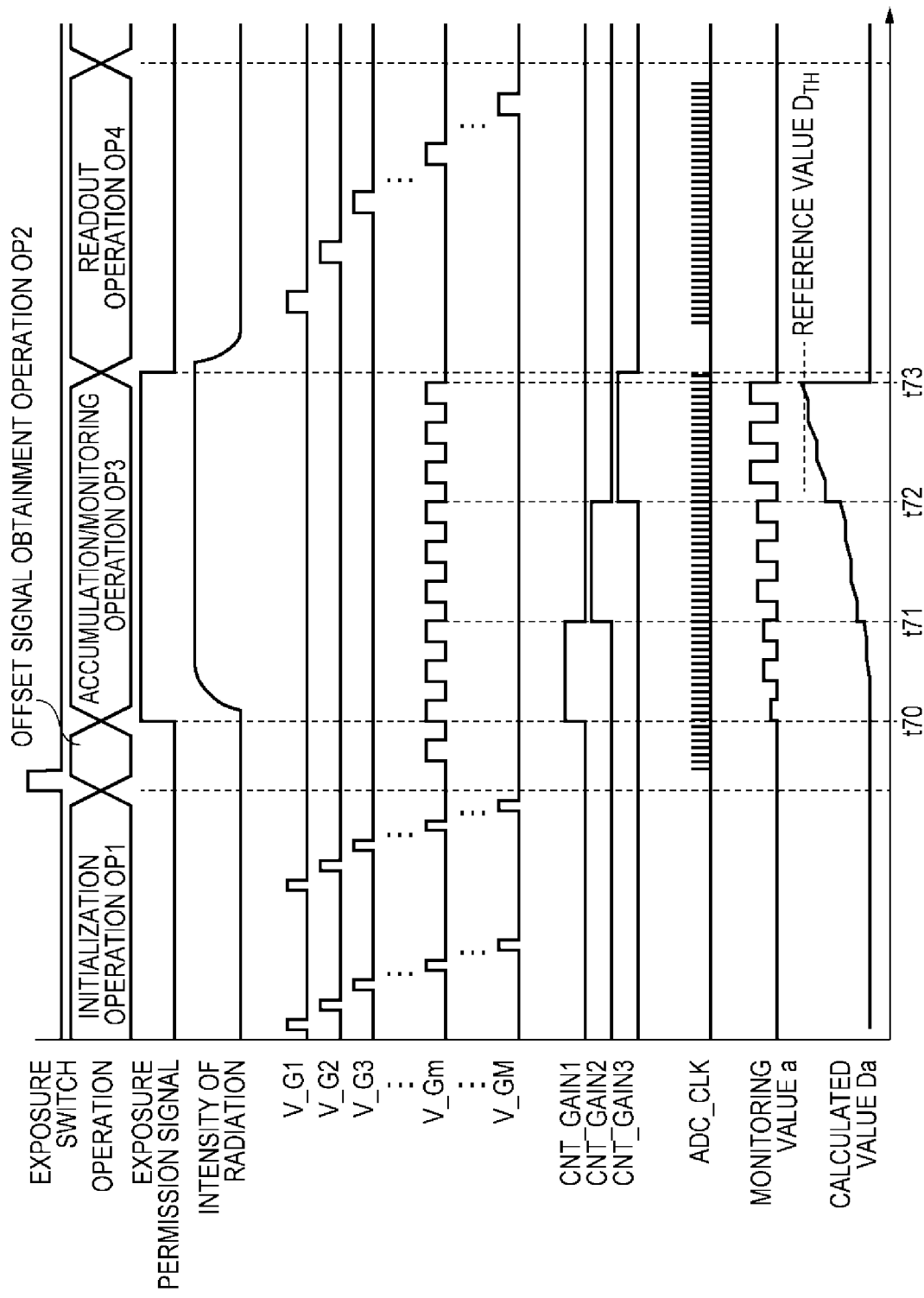
[Fig. 7]

RADIATION IMAGING APPARATUS, CONTROL METHOD THEREOF AND RADIATION IMAGING SYSTEM

TECHNICAL FIELD

The present invention relates to a radiation imaging apparatus and a control method thereof.

BACKGROUND ART

A radiation imaging apparatus includes, for example, a plurality of sensors arrayed so as to form a plurality of rows and a plurality of columns, a drive unit which drives each sensor row by row, and a readout unit which reads out a signal from each driven sensor.

In Japanese Patent Laid-Open No. 2013-98796, the start of radiation irradiation is detected based on signals from some of the plurality of sensors and the end of radiation irradiation is detected based on the signals from the some sensors in the radiation imaging apparatus. According to Japanese Patent Laid-Open No. 2013-98796, signals are read out from some of the sensors while maintaining the operation mode of the readout unit to have a mode with a high signal amplification ratio in order to improve the detection accuracy of the start of radiation irradiation. Then, after the start of radiation irradiation is detected, the operation mode of the readout unit is changed to a mode with a low signal readout ratio to prevent the saturation of the signals that have been read out from some of the sensors.

Some radiation imaging apparatuses can monitor the radiation dose and cause radiation irradiation to end (for example, output, to the radiation source, a signal to stop radiation irradiation) when the dose reaches a target value. This operation is called Automatic Exposure Control (AEC) and can, for example, prevent excessive radiation irradiation.

In Japanese Patent Laid-Open No. 2010-75556, some sensors are used as monitoring sensors to monitor the radiation dose, the signals of the monitoring sensors are monitored after the start of radiation irradiation, and radiation irradiation is ended based on the monitoring result. Additionally, in Japanese Patent Laid-Open No. 2010-75556, the signals of the monitoring sensors are monitored at least twice, and the timing to end radiation irradiation is determined based on these timings and theses monitoring results.

Generally, when the intensity of radiation is comparatively high (or low), the time until the radiation dose can reach the target value can be considered to become short (or long) and requires AEC of a given intensity of radiation to be properly performed in a radiation imaging apparatus. However, in a case in which the intensity of radiation is higher than an assumed value or in a case in which the signal amplification ratio of the readout unit is not properly set, the output value of the readout unit may become saturated (may exceed the output dynamic range).

According to the AEC method of Japanese Patent Laid-Open No. 2010-75556, radiation irradiation cannot be properly ended or the timing to end the radiation irradiation cannot be properly determined when the output value (monitoring result) of the readout unit becomes saturated. As a result, the accuracy of AEC is decreased. Also, if the signal amplification ratio of the readout unit is changed in accordance with the method of Japanese Patent Laid-Open No. 2013-98796 while AEC is being performed, the output value of the readout unit is changed by the change. Therefore, radiation irradiation cannot be properly ended or the timing to end the radiation irradiation cannot be properly determined, and as a result the accuracy of AEC is decreased even by the method of Japanese Patent Laid-Open No. 2013-98796.

SUMMARY OF INVENTION

The present invention has been made in recognition of the above problem by the inventor and provides a technique advantageous in increasing the accuracy of the AEC.

One of the aspects of the present invention provides a radiation imaging apparatus that includes a plurality of sensors arrayed on a substrate, a drive unit, a readout unit, and a control unit, wherein the control unit performs a first control of reading out by the readout unit, after radiation irradiation is started to the plurality of sensors, signals from some of the sensors which have been driven out of the plurality of sensors by driving the some of the sensors by the driving unit, and a second control of outputting a control signal to end radiation irradiation when a calculated value calculated based on an output of the readout unit in the first control reaches a reference value, operation modes of the readout unit include a plurality of modes having different signal amplification ratios from each other, and the control unit reads out, in the first control, the signals from the some of the sensors by changing an operation mode of the readout unit so a value of an output of the readout unit is not saturated, and calculates, in the second control, the calculated value as a value that indicates a radiation dose by accumulating the output of the readout unit in consideration of the signal amplification ratio of the readout unit.

Further features of the present invention will become apparent from the following description of exemplary embodiments with reference to the attached drawings.

BRIEF DESCRIPTION OF DRAWINGS

FIG. 1 is a block diagram for explaining an example of the configuration of an imaging system;

FIG. 2 is a block diagram for explaining an example of the configuration of a radiation imaging apparatus;

FIG. 3 is a timing chart for explaining a reference example of an AEC operation;

FIG. 4 is a graph for explaining a crosstalk component included in a signal read out from a monitoring sensor;

FIG. 5 is a view for explaining an example of the configuration of a readout unit;

FIG. 6 is a flowchart for explaining an example of the AEC operation; and

FIG. 7 is a timing chart for explaining an example of the AEC operation.

DESCRIPTION OF EMBODIMENTS

FIG. 1 shows a configuration example of an imaging system SYS to perform radiation imaging. The imaging system SYS includes a radiation imaging apparatus 100, a processor 200, a radiation controller 300, and a radiation source 400. The processor 200 controls the radiation imaging apparatus 100 and radiation controller 300 based on, for example, imaging conditions input by the user via a terminal 210. The radiation controller 300 drives the radiation source 400 based on a signal from the processor 200, and the driven radiation source 400 generates radiation (for example, an X-ray, α-ray, or β-ray). The radiation is transmitted through an object to be examined (not shown), and the radiation imaging apparatus 100 detects this radiation containing information of the object to be examined. The radiation imaging apparatus 100 generates image data based on the detected radiation, and outputs the image data to the processor 200. The processor 200 outputs a radiation image based on the image data to a display unit 220 such as a display.

The radiation imaging apparatus 100 includes a sensor array 110, a drive unit 120, a readout unit 130, a processor 140, a hold unit 150, a communication unit 160, a control unit 170, and a power supply unit 180.

The sensor array 110 includes a plurality of sensors so arranged as to form a plurality of rows and a plurality of columns on a substrate. Each sensor includes a detecting element for detecting radiation and can include, for example, a photoelectric conversion element (PIN photodiode, MIS sensor or the like) formed by amorphous silicon on an insulating substrate such as a glass substrate. In this case, a scintillator for converting radiation into light can be arranged on the side of an irradiation surface of the sensor array 110.

The drive unit 120 drives the sensors of the sensor array 110 row by row. The drive unit 120 includes a scanning circuit formed by using, for example, shift registers, and sequentially selectively drives the sensors on each row. The readout unit 130 reads out a signal from each of a plurality of sensors driven by the drive unit 120. The value of this signal corresponds to the radiation dose detected by the corresponding sensor. In this example, the signal value corresponds to the quantity of light that has entered the corresponding sensor from the scintillator.

The processor 140 is formed by an integrated circuit such as an ASIC, generates image data based on a signal read out by the readout unit 130, and performs data processing such as a correction process on the image data. The hold unit 150 is a memory for holding image data, and it is possible to use, for example, a volatile memory such as a DRAM, a non-volatile memory such as a flash memory, or another known storage means. The communication unit 160 is an external interface for exchanging signals and data with the processor 200, and it is possible to use a wired communicating means or wireless communicating means. The communication unit 160 may also exchange signals and data with another unit (not shown).

To properly perform radiation imaging, the control unit 170 controls the operations of the above-mentioned units forming the radiation imaging apparatus 100, for example, controls synchronization of these units by using a reference signal such as a clock signal. The power supply unit 180 supplies electrical power to each unit so that the unit properly operates. For example, the power supply unit 180 generates one or more voltages based on external electrical power, and supplies each generated voltage to a corresponding unit.

The radiation imaging apparatus 100 starts radiation imaging upon detecting the start of radiation irradiation. For example, an exposure switch (not shown) is connected to the radiation control unit 300, and a signal indicating the start of radiation irradiation is supplied to the radiation imaging apparatus 100 in response to the user pressing the exposure switch. Upon receiving the signal indicating the start of radiation irradiation, the radiation imaging apparatus 100 outputs, to the radiation control unit 300, an exposure permission signal that indicates permission to start and a request to start radiation irradiation after a predetermined operation has been performed. The radiation control unit 300 drives the radiation source 400 upon receiving the exposure permission signal. Note that the method of detecting the start of radiation irradiation of the radiation imaging apparatus 100 is not limited to the above-described example. For example, a sensor dedicated to detecting the start of radiation irradiation can be provided in the radiation imaging apparatus 100 or another known arrangement for detecting the start of radiation irradiation by the radiation imaging apparatus 100 itself may be provided.

The configurations of the imaging system SYS and radiation imaging apparatus 100 are not limited to the above-described examples, and the arrangements of the aforementioned units can appropriately be changed. For example, a part of the function of a given unit may also be achieved by another unit, and the functions of two more units may also be achieved by one unit. For example, a part of the function of the processor 140 may also be implemented by the processor 200, and the processor 140 and processor 200 may also be formed by a single unit.

FIG. 2 shows a configuration example of the sensor array 110 and readout unit 130. In this example, the sensor array 110 includes a plurality of sensors PX (PX_11, PX_12, . . . , PX_MN) so arranged as to form M rows and N columns. The sensor PX may also be referred to as a "pixel".

For example, the sensor PX_11 positioned in the first row and first column includes a photoelectric conversion element S and thin-film transistor W. For example, one terminal of the photoelectric conversion element S is connected to the thin-film transistor W, and the other terminal thereof is connected to a power line for propagating a reference voltage VS received from the power supply unit 180. The thin-film transistor W is turned on or off in response to a signal received from the drive unit 120 via a signal line G1. While the thin-film transistor W is kept off, electric charge is stored in the photoelectric conversion element S. When the thin-film transistor W is turned on, a signal corresponding to the amount of accumulated charge is transferred to the readout unit 130 via a corresponding column signal line L1. This applies to other sensors PX_12, . . . , PX_MN.

The readout unit 130 includes signal amplifying units 131, sampling units 132, a scanning circuit 133, and an output unit 134. The signal amplifying units 131 are arranged in one-to-one correspondence with the columns, and each amplify signals from corresponding sensors PX. For example, the signal amplifying unit 131 can include an integral amplifier, a variable amplifier, or another known signal amplifying circuit. The sampling units 132 are arranged in one-to-one correspondence with the columns, and each sample a signal from a corresponding signal amplifying unit 131. The sampling unit 132 can include a switching element and a capacitor, and can further include a buffer amplifier for amplifying the sampled signal. The scanning circuit 133 is formed by using shift registers or the like, and supplies a control signal to the sampling unit 132 corresponding to each column. In response to this control signal from the scanning circuit 133, the sampling unit 132 transfers the sampled signal to the output unit 134. The output unit 134 includes an output circuit for outputting the sampled signal to an external unit (for example, the processor 140). For example, the output unit 134 can include a buffer amplifier and A/D converter.

The processor 140 processes the signals from the plurality of sensors PX read out by the readout unit 130, as image data of one frame. That is, image data of one frame is obtained by reading out signals from the plurality of sensors PX once.

A reference example of AEC (Automatic Exposure Control) in the radiation imaging apparatus 100 will be described with reference to FIG. 3. FIG. 3 shows a timing chart of an AEC operation. In FIG. 3, the abscissa indicates the time. In FIG. 3, the ordinate indicates the exposure switch, the operation, the exposure permission signal, the intensity of radiation, signals such as V_G1 (V_G1, V_G2, . . . , V_GM), a clock signal ADC_CLK, a monitoring value a, and a calculated value Da.

"Exposure switch" in FIG. 3 indicates a signal from the exposure switch (not shown) connected to the radiation control unit 300. In FIG. 3, L level indicates that the exposure switch has not been pressed and H level indicates that the exposure switch has been pressed.

"Operation" in FIG. 3 indicates each operation which is to be performed in the radiation imaging apparatus 100 at the time of radiation imaging and corresponds to the operation mode or state of the radiation imaging apparatus 100. Although details will be described later, an initialization operation OP1 is performed first, the initialization operation OP1 is stopped in response to the pressing of the exposure switch, and an offset signal obtainment operation OP2 is performed. Next, an accumulation/monitoring operation OP3 is performed along with the start of radiation irradiation. Subsequently, the accumulation/monitoring operation OP3 is stopped in accordance with the end of radiation irradiation, and a readout operation OP4 is performed.

"Exposure permission signal" in FIG. 3 is a signal that is output from the radiation imaging apparatus 100 to the radiation control unit 300 and indicates permission to start and a request to start radiation irradiation. Upon receiving the exposure permission signal from the radiation imaging apparatus 100, the radiation control unit 300 starts radiation irradiation by driving the radiation source 400. In FIG. 3, L level indicates a state in which the start of radiation irradiation has not been permitted (requested), and H level indicates a state in which the start of radiation irradiation is permitted.

"Intensity of radiation" in FIG. 3 indicates the intensity of radiation irradiation or the irradiation rate. That is, the intensity of radiation indicates the radiation dose per each unit time, and a result obtained from time-integrating the intensity of radiation becomes the radiation dose. In FIG. 3, L level indicates a state in which no radiation irradiation is performed and H level (and a level midway between L level to H level) indicates a state in which radiation irradiation is being performed.

"V_G1" in FIG. 3 is a control signal propagating in the signal line G1 (Refer to FIG. 2). If the signal V_G1 is activated, the first row sensors PX_11 to PX_1N are driven. That is, when the signal V_G1 shifts to H level, the transistors W of the respective first row sensors PX_11 to PX_1N become electrically conductive, and the signals of the respective photoelectric conversion elements S are transferred via the corresponding column signal lines such as L1 and the like to the readout unit 130. The same operation is performed for other signals V_G2 to V_GM.

"ADC_CLK" in FIG. 3 indicates a clock signal used to A/D-convert the signals from the sensors PX. The clock signal ADC_CLK is supplied to, for example, an A/D converter included in the output unit 134. "Monitoring value a" in FIG. 3 indicates the output from the readout unit 130 during the accumulation/monitoring operation OP3. In this example, a numerical value corresponding to the aforementioned A/D converted digital value is indicated as the monitoring value a. Note that the monitoring value a does not include the outputs from the readout unit 130 during the initialization operation OP1 and the readout operation OP4. "Calculated value Da" in FIG. 3 is a value obtained by accumulating the monitoring values a and can be referred to as an "integrated value" or an "integral value".

First, the initialization operation OP1 is performed before the start of radiation irradiation and before the exposure switch is pressed. The initialization operation OP1 can be performed by repeatedly performing activation by activating the signals V_G1, V_G2, . . . , V_GM in this order (setting the thin film transistors W in an electrically conductive state) in a state in which the column signal lines L1 to LN are fixed to a constant potential. Accordingly, charges due to a dark current of the substrate are removed from each photoelectric conversion element S and the potential of each photoelectric conversion element S is initialized. Note that the initialization method and the configuration for initialization are not limited to the above-described example, and a reset transistor may be provided for each sensor PX or another known initialization means can be used.

Next, in response to the pressing of the exposure switch, the initialization operation OP1 is ended and the offset signal obtainment operation OP2 is started. The offset signal obtainment operation OP2 is performed by reading out signals from some of the plurality of sensors PX under a state in which the sensor array 110 is not irradiated with radiation. More specifically, letting m be a given integer from 1 to M, the signal VG_M is activated to drive each of the mth row sensors PX_m1 to PX_mN. The signals read out by the readout unit 130 from the respective mth row sensors PX_m1 to PX_mN can be used to perform offset correction on the monitoring value a which is to be read out in the accumulation/monitoring operation OP3 (to be described later).

After the offset signal obtainment operation OP2 is ended, the accumulation/monitoring operation OP3 is started upon output of the exposure permission signal to the radiation control unit 300. In the accumulation/monitoring operation OP3, charges are accumulated in the plurality of sensors PX and the accumulated charge amount of some of the plurality of sensors PX is monitored by reading out signals in a predetermined cycle from some of the plurality of sensors PX. More specifically, a signal V_GM is activated at a predetermined cycle to drive the mth row sensors PX_m1 to PX_mN. The signals from the respective mth row sensors PX_m1 to PX_mN that have been driven are read out by the readout unit 130 as the above-described monitoring values a.

That is, during the accumulation/monitoring operation OP3, each of the mth row sensors PX_m1 to PX_mN can be represented as a sensor which functions as a monitoring sensor to monitor the radiation dose or the longitudinal changes of the radiation dose. Note that although, in this configuration example, the above-described monitoring value a is a value obtained by amplifying a monitoring sensor signal by the corresponding signal amplification unit 131, sampling the amplified signal by the corresponding sampling unit 132, and outputting the sampled signal to the output unit 134, it need only be a value corresponding to the value of the monitoring sensor signal.

When the calculated value Da which is the accumulated value of the monitoring values a reaches a reference value $D_{TH}$ (the reference value $D_{TH}$ is a value corresponding to a target value, an allowable value, and an upper limit value or the like of the radiation dose and can be, for example, preset by the user), the aforementioned exposure permission signal is set at a logic level to end radiation irradiation. In this manner, AEC is performed and radiation irradiation is stopped.

In addition, in response to the calculated value Da reaching the reference value $D_{TH}$, the accumulation/monitoring operation OP3 is ended and the readout operation OP4 is started. In the readout operation OP4, the signals V_G1, VG_2, . . . , VGM are activated in this order (setting the respective thin film transistors W to an electrically conductive state), and signals are read out from the plurality of sensors PX by the readout unit 130. The processor 140 generates image data based on the readout signals.

Note that for each of the signals V_G1 and the like, the pulse width in the initialization operation OP1, the pulse width in the accumulation/monitoring operation OP3, and the pulse width in the readout operation OP4 can be different from each other, but may be equal to each other or some may be equal to each other.

The signal read out from each of the mth row sensors PX_m1 to PX_mN in the readout operation OP4 has lost a part of its signal component due to the signal being read out as the monitoring value a during the accumulation/monitoring operation OP3. Therefore, it is preferable to add the calculated value Da which is the accumulated value of the monitoring value a to each signal read out from each of the mth row sensors PX_m1 to PX_mN during the readout operation OP4. In another example, each signal read out from each of the mth row sensors PX_m1 to PX_mN can be corrected based on signals read out from the sensor PXs of an adjacent row ((m−1)th row and or (m+1)th row). In yet another example, each signal read out from each of the mth row sensors PX_m1 to PX_mN can be complemented by signals read out from the adjacent row sensor PX.

When reading out signals from the respective mth row sensors PX_m1 to PX_mN during the accumulation/monitoring operation OP3, even if the thin film transistors W of sensors PX (to be referred to as non-monitoring target sensors" hereinafter) of other rows are set to a non-conductive state, noise from the non-monitoring target sensors PX can mix into the column signal line L1 and the like. That is, since the thin film transistor W of each non-monitoring target sensor PX is set to a non-conductive state, the signal corresponding to the accumulated charge amount of each non-monitoring target sensor PX is not directly transferred to the corresponding column signal line L1 or the like. However, a change in the potential of the photoelectric conversion element which occurs along with the accumulation of charges in each non-monitoring target sensor PX can propagate as noise in the corresponding column signal line L1 or the like due to capacitive coupling formed between the electrode of the photoelectric conversion element S and the corresponding column signal line L1 or the like.

The above-described noise can also be referred to as "crosstalk". In general, since the number of the above-described non-monitoring target sensors is larger than the number of monitoring sensors (the number of sensors which are monitoring targets), when a signal is read out from each monitoring sensor, a substantial amount of crosstalk can mix with the signal. Particularly, since the amount of change of the potential of each photoelectric conversion element S can increase along with the increase in the intensity of radiation, higher the intensity of radiation, the greater the crosstalk will be.

FIG. 4 is a graph for explaining the crosstalk component included in the signal read out from each monitoring sensor. The abscissa indicates the radiation irradiation time [msec] and the ordinate indicates the monitoring value or the signal value.

Here, a case in which the radiation dose is fixed to a constant value (for example, 15,000 [LSB]) will be considered. For example, assume that the intensity of radiation is 15,000 [LSB/msec] for an irradiation time of 1 [msec]. For example, assume that the intensity of radiation is 1,500 [LSB/msec] for an irradiation time of 10 [msec]. For example, assume that the intensity of radiation is 150 [LSB/msec] for an irradiation time of 100 [msec]. In FIG. 4, a signal value SS read out from each unit sensor PX during the readout operation OP4 indicates a value equivalent to 15,000 [LSB] in any of the irradiation times.

Letting "monitoring value S0" be the monitoring value (a signal value read out via one corresponding column signal line during the accumulation/monitoring operation OP3) for each unit column in the above described conditions, a crosstalk component SC in FIG. 4 indicates the crosstalk component included in the monitoring value S0. A signal component SA in FIG. 4 indicates a component obtained by subtracting the crosstalk component SC from the monitoring value S0 (that is, SA=S0−SC). Additionally, an output saturation value $S_{SAT}$ in FIG. 4 indicates the output saturation value (more specifically, for example, the upper limit of the output value of either the signal amplification units 131, the sampling units 132, or the output unit 134) of the readout unit 130. The output saturation value $S_{SAT}$ is equivalent to approximately 40,000 [LSB].

According to FIG. 4, the signal component SA increases when the irradiation time is decreased (when the intensity of radiation is increased), and the signal component SA decreases when the irradiation time is increased (when the intensity of radiation is decreased). Additionally, in the same manner as the signal component SA, the crosstalk component SC increases when the irradiation time is decreased (when the intensity of radiation is increased), and the crosstalk component SC decreases when the irradiation time is increased (when the intensity of radiation is decreased). According to FIG. 4, the signal component SA is smaller than the crosstalk component SC by two orders of magnitude.

The signal component SA can be obtained by subtracting the crosstalk component SC from the monitoring value S0. For example, in the aforementioned reference example (refer to FIG. 3), the crosstalk component SC can be obtained from the output from the readout unit 130 between readout operations of the monitoring values a during the accumulation/monitoring operation OP3. That is, the crosstalk component SC can be the output of the readout unit 130 from a period in between a readout operation of the monitoring value a performed at a given timing and the next read out operation of the monitoring value a performed in the subsequent timing (a period when the thin-film transistors W of the respective monitoring sensors are in a non-conductive state). This allows the output of the readout unit 130 to be obtained as the crosstalk component SC in a state where the crosstalk component, which has mixed into the column signal line L1 or the like, has at least not disappeared. Preferably, the output from the readout unit 130 substantially immediately after the readout operation of the monitoring values a can be the crosstalk component SC. This allows the output of the readout unit 130 to be obtained as the crosstalk component SC in a state almost equal to or at least close to the state immediately after the crosstalk component has mixed into the column signal line L1 or the like. As a result, the signal component SA can be calculated with high accuracy. Although the crosstalk component SC can be measured by the aforementioned method, it may also be pre-obtained for each imaging condition (for example, for each irradiation time or intensity of radiation) or may be calculated based on the circuit configuration of the sensor array 110 and its structure.

Here, for example, if the irradiation time is shorter than T1 in FIG. 4, that is, if monitoring value S0=SA+SC becomes larger than the output saturation value $S_{SAT}$, signals (S0−$S_{SAT}$) equivalent to the amount that has exceeded the output saturation value $S_{SAT}$ will be lost. Therefore, in such a case, the accuracy of AEC will be reduced since the signal component SA cannot be properly calculated by the aforementioned method. An example of AEC which is advantageous in increasing the accuracy of AEC will be described below with reference to FIGS. 5 to 7.

FIG. 5 is a view for explaining a detailed configuration example of the signal amplification units 131, the sampling units 132, and the output unit 134 of the readout unit 130.

Each signal amplification unit 131 includes, for example, a differential amplifier A1, feedback capacitors C_FB1 to C_FB3, and switch elements SW_FB1 to SW_FB3 and SW_RES. The non-inverting input terminal ("+" terminal in FIG. 5) of the differential amplifier A1 is supplied with, for example, a constant voltage VREF (a target voltage or a reference voltage). The feedback capacitor C_FB1 and the switch element SW_FB1 are arranged in series on a first path that connects the inverting input terminal ("−" terminal in FIG. 5) and the output terminal of the differential amplifier A1. The feedback capacitor C_FB2 and the switch element SW_FB2 are arranged in series on a second path that connects the inverting input terminal and the output terminal of the differential amplifier A1. The feedback capacitor C_FB3 and the switch element SW_FB3 are arranged in series on a third path that connects the inverting input terminal and the output terminal of the differential amplifier A1. In addition, the switch element SW_RES is arranged in series on a fourth path that connects the inverting input terminal and the output terminal of the differential amplifier A1. Note that the above-described first to fourth paths have a relationship in which they are parallel to each other.

Each signal amplification unit 131 includes a plurality of operation modes having different signal amplification ratios (gains) from each other and can change the signal amplification ratio by controlling the switch elements SW_FB1 to SW_FB3. For example, out of the switch elements SW_FB1 to SW_FB3, the signal amplification ratio of each signal amplification unit 131 increases in the order when the switch element SW_FB1 is set to an electrically conductive state, when the switch element SW_FB2 is set to an electrically conductive state, and when the switch element SW_FB3 is set to an electrically conductive state. In addition, each signal amplification unit 131 can be initialized by setting the switch element SW_RES in an electrically conductive state.

Note that, although an example in which one ratio out of three signal amplification ratios is selected has been shown here, but the number of selectable signal amplification ratios can be two or may be four or more. In addition, another signal amplification ratio can be set by selectively setting at least two switch elements out of the switch elements SW_FB1 to SW_FB3 in an electrically conductive state.

Each sampling unit 132 includes, for example, a resistance element RO, sampling switch elements SW_SH1 and SW_SH2, sampling capacitors C_SH1 and C_SH2, and a multiplexer MUX. The resistance element RO forms a part of the low-pass filter to block a high frequency component signal (noise). The switch element SW_SH1 connects the resistance element RO and the sampling capacitor C_SH1. The switch element SW_SH1 and the sampling capacitor C_SH1 sample a signal (a signal (S signal) equivalent to the signal component) from the corresponding signal amplification unit 131. More specifically, the sampling capacitor C_SH1 is charged with a voltage corresponding to the signal from the corresponding signal amplification unit 131 when the switch element SW_SH1 is set to an electrically conductive state. Then, the voltage becomes fixed to the sampling capacitor C_SH1 when the switch element SW_SH1 is subsequently set to a non-conductive state. The switch element SW_SH2 and the sampling capacitor C_SH2 perform the same operation as the switch element SW_SH1 and the sampling capacitor C_SH1 and sample a signal (a signal (N signal) equivalent to the noise component) from the corresponding signal amplification unit 131. The multiplexer MUX transfers the sampled signal (described above) to the output unit 134 based on the control signal from the scanning circuit 133.

The output unit 134 includes a differential amplifier A2 and an A/D converter ADC. The differential amplifier A2 amplifies the difference between the S signal and the N signal transferred by the multiplexer MUX. The A/D converter ADC A/D converts each signal from the differential amplifier A2 based on the aforementioned clock signal ADC_CLK.

FIG. 6 is a flowchart showing an example of the AEC operation during the accumulation/monitoring operation OP3. In step S100 (to be simply referred to as "S100" hereinafter; this applies to other steps), the start of radiation irradiation is requested, that is, the exposure permission signal to be output to the radiation control unit 300 is set to H level.

In S110, it is determined whether the monitoring values a have reached a reference value A1. If a≥A1, the process advances to S115. If a<A1, the process advances to S120. The reference value A1 corresponds to the output saturation value $S_{SAT}$ described with reference to FIG. 4. In S115, the signal amplification ratios of the respective signal amplification units 131 are lowered by one level by controlling the corresponding switch elements SW_FB1 to SW_FB3 which were described with reference to FIG. 5, and the process returns to S110. Furthermore, in S115, the user may be notified of the saturation of monitoring value a. The processes of S110 and S115 attempt to prevent the monitoring values a from being saturated.

When changing the signal amplification ratio of each signal amplification unit 131, the calculated value Da which is the accumulated value of the monitoring values a can be corrected based on the changed signal amplification ratio. If the signal amplification ratio is changed, a signal value amplified by a signal amplification ratio different from a previous ratio will be subsequently added to the calculated value Da that has been obtained up to that point. Therefore, the calculated value Da that has been obtained before the change can be, for example, corrected based on a ratio between the pre-change signal amplification ratio and the post-change signal amplification ratio. This can be applied in the same manner when the signal amplification ratio of each signal amplification unit 131 is to be changed in other steps to be described later.

In S120, it is determined whether monitoring value a has reached a reference value A2 (<A1). If a≥A2, the process advances to S125. If a<A2, the process advances to S130. The reference value A2 indicates the first warning level that there is possibility that the monitoring value a may become saturated. In S125, the signal amplification ratio of each signal amplification unit 131 is decreased by one level by controlling the corresponding switch elements SW_FB1 to SW_FB3, and the process returns to S120. The possibility that the monitoring value a will become saturated is reduced by the processes of S120 and S125.

For example, in a case where the intensity of radiation is comparatively high, the radiation dose can be considered to reach its target value in a comparatively short amount of time since the start of radiation irradiation. On the other hand, however, there is a possibility that the monitoring value a will become saturated in this comparatively short amount of time. Hence, the signal amplification ratio of each signal amplification unit 131 is preferably set low in the corresponding periods immediately before and after radiation irradiation is started by the processes of the above-described S110 to S125.

In S130, it is determined whether the intensity of radiation has stabilized (whether it has become a steady state). If the intensity of radiation has stabilized, the process advances to S140. Otherwise, the process returns to S120. The determination can be performed based on whether the change amount of the monitoring value a (more specifically, the difference between the monitoring value a from a monitoring operation performed at a given timing and the monitoring value a from a monitoring operation performed at a subsequent timing) has become less than a predetermined amount.

In S140, the signal amplification ratio of each signal amplification unit 131 is increased by one level by controlling the switch elements SW_FB1 to SW_FB3, and the process advances to S150. As described with reference to FIG. 4, the signal component SA is much smaller than the crosstalk component SC. Hence, the detection accuracy of the signal component SA can be made higher by increasing the signal amplification ratio by this process.

In S150, it is determined whether the monitoring value a is less than a reference value A3 (<A2). If a≥A3, the process advances to S160. If a<A3, the process advances to S155. The reference value A3 indicates, for example, the second warning level that there is a possibility that the monitoring value a will be smaller than the noise component. In S155, the signal amplification ratio of each signal amplification unit 131 is increased by one level by controlling the switch elements SW_FB1 to SW_FB3, and the process returns to S150. The processes of S150 and S155 can prevent the monitoring value a from not being properly obtained due to the noise component, thereby preventing a reduction in the accuracy of AEC.

In S160, it is determined whether the calculated value Da has reached the reference value $D_{TH}$. If Da≥$D_{TH}$, the process advances to S170. If Da<$D_{TH}$, the process returns to S150. In this embodiment, for example, if the signal amplification ratio of each signal amplification unit 131 has been changed in the above-described S115, S125, S140, and S155, the reference value $D_{TH}$ is changed based on the changed signal amplification ratio or set to a value corresponding to the changed signal amplification ratio. In S170, the end or stop of radiation irradiation is requested, that is, the exposure permission signal output to the radiation control unit 300 is set to L level.

Note that the AEC operation according to the present invention is not limited to the example of the above-described flowchart and can be partially changed without departing from the spirit or scope of the present invention. For example, some of the above-described steps may be omitted or other steps may be added as needed.

FIG. 7 is a timing chart showing an example of the AEC operation according to the present invention. The embodiment differs from that of the reference example (refer to FIG. 3) in the point that the accumulation/monitoring operation OP3 is performed by changing the signal amplification ratio of each signal amplification unit 131 so the monitoring value a will not be saturated.

"CNT_GAIN1" to "CNT_GAIN3" in FIG. 7 correspond to the switch elements SW_FB1 to SW_FB3, respectively. For example, when the control signal CNT_GAIN1 is set to H level, the switch element SW_FB1 is set to an electrically conductive state, and a first signal amplification ratio which is the lowest signal amplification ratio of the embodiment is set. When the control signal CNT_GAIN2 is set to H level, a second signal amplification ratio which is higher than the above-described first signal amplification ratio is set. Additionally, when the control signal CNT_GAIN3 is set to H level, a third signal amplification ratio which is the highest signal amplification ratio of the embodiment is set as the signal amplification ratio. Referring to FIG. 7, at times t70 and t71, the control signal CNT_GAIN1 is set to H level, and the first signal amplification ratio is set. At times t71 and t72, the control signal CNT_GAIN2 is set to H level, and the second signal amplification is set. Additionally, at time t72 and t73, the control signal CNT_GAIN3 is set to H level, and the third signal amplification ratio is set. Although the example of FIG. 7 shows a mode in which the signal amplification ratio is gradually increased after radiation irradiation is started, the signal amplification ratio can be decreased as needed in accordance with the example of the flowchart of FIG. 6.

As shown in FIG. 7, at times t71 and t72 which are timings that the signal amplification ratio is changed, the calculated value Da can be corrected based on the changed signal amplification ratio. This is because, as mentioned above, when the signal amplification is changed, signal values that have been amplified by a signal amplification ratio different from a prior ratio are accumulated on the calculated value Da obtained up to that point.

According to the embodiment, the accumulation/monitoring operation OP3 is performed by changing the signal amplification ratio of each signal amplification unit 131 so the monitoring value a will not be saturated. When the signal amplification ratio is changed, the calculated value Da is corrected based on the changed signal amplification ratio. Hence, according to the embodiment, the comparison between the calculated value Da and the reference value $D_{TH}$ can be properly performed, and radiation irradiation can be properly ended when the comparison result is Da≥$D_{TH}$. Therefore, the embodiment is advantageous in increasing the accuracy of AEC.

Although a mode in which AEC is performed by using the calculated value Da which is the accumulated value of the monitoring values a has been considered above, it is possible to partially change and combine the mode without departing from the scope and spirit of the invention. For example, AEC can be performed by using a result obtained by accumulating only some of the monitoring values a. More specifically, only some of the mth row sensors PX can be made to function as monitoring sensors, that is, only some of the signals out of the signals of the mth row sensors PX can be adopted as the monitoring values a. In another example, AEC can be performed by causing the sensors PX of two or more rows including the mth row and another row to function as the monitoring sensors. In yet another example, AEC can be performed by causing only some of the sensors PX corresponding to a portion, out of a region on a sensor array 110, where the radiation does not pass through an object to be examined (or a portion having a high likelihood that the radiation will not pass) or another portion of interest to a user to function as the monitoring sensors. Furthermore, in another example, a component corresponding to the signal component SA out of the monitoring value a can be calculated, and AEC can be performed by using a result obtained by accumulating the calculated components. Alternatively, AEC can be performed by combining these examples.

In addition, although the above description has paid attention to the occurrence of crosstalk during the accumulation/monitoring operation OP3, the present invention can be applied to increase the accuracy of AEC by preventing the output saturation of the readout unit 130 that could occur due to other reasons.

Furthermore, although the embodiment of the present invention has been described by using the calculated value Da, which is an accumulated value of the monitoring values a, for the sake of comparison with the aforementioned reference example, the embodiment may be implemented by a more generalized mode. That is, the calculated value Da can be calculated by being converted into a value that can be directly compared with the target value of the radiation dose or a value corresponding to the target value. In this case, the calculated value Da can be obtained by performing weighted addition to the monitoring value a based on the signal amplification ratio of each signal amplification unit 131 and accumulating the monitoring values a in consideration of the signal amplification ratio. Additionally, in this case, the reference value $D_{TH}$ can be a predetermined value (a target value of the radiation dose or a corresponding fixed value) regardless of the signal amplification ratio.

The present invention is not limited to the above described embodiments and their modifications, and the embodiments may be partially changed without departing from the scope or spirit of the present invention. For example, although each of the above-described embodiments referred to a so-called "indirect conversion type" arrangement which converts the radiation into light by a scintillator and converts the converted light into an electrical signal by a sensor, the present invention can also be applied to a so-called "direct conversion type" arrangement which directly converts the radiation into an electrical signal.

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2015-133921, filed Jul. 2, 2015, which is hereby incorporated by reference herein in its entirety.

The invention claimed is:

1. A radiation imaging apparatus, comprising:
a plurality of sensors arrayed on a substrate;
a drive unit;
a readout unit; and
a control unit, wherein the control unit is configured to perform a first control of reading out by the readout unit, after radiation irradiation from a radiation source is started to the plurality of sensors, signals from some of the plurality of sensors that have been driven out by driving the some of the sensors by the driving unit,
the control unit is further configured to perform a second control of outputting a control signal to end the radiation irradiation from the radiation source when a value calculated based on an output of the readout unit in the first control reaches a reference value,
operation modes of the readout unit include a plurality of modes having different signal amplification ratios from each other,
the control unit reads out the signals from the some of the sensors in the first control by changing an operation mode of the readout unit such that a value of an output of the readout unit is not saturated, and
the control unit calculates the calculated value to indicate a radiation dose in the second control by accumulating the output of the readout unit in consideration of the signal amplification ratio of the readout unit.

2. The apparatus according to claim 1, wherein the control unit is further configured to perform a third control of reading out, by the readout unit, signals from the plurality of sensors after radiation irradiation is ended by the second control.

3. The apparatus according to claim 1, wherein the control unit is further configured to change the operation mode of the readout unit in the first control so as to set a lower signal amplification ratio than the signal amplification ratio of the readout unit when the value of the output of the readout unit is larger than a first reference value, and to change the operation mode of the readout unit so as to set a higher signal amplification ratio than the signal amplification ratio of the readout unit when the value of the output of the readout unit is smaller than a second reference value that is smaller than the first reference value.

4. The apparatus according to claim 3, wherein the control unit is further configured to change the operation mode of the readout unit in the first control so as to set a higher amplification ratio than the signal amplification ratio of the readout unit when the output of the readout unit is set to a steady state.

5. The apparatus according to claim 4, wherein the control unit is further configured to change the operation mode of the readout unit in the first control so as to set a higher signal amplification ratio than the signal amplification ratio of the readout unit when an output change amount of the readout unit becomes smaller than a predetermined amount.

6. The apparatus according to claim 1, wherein the control unit is configured to output the control signal in the second control when the calculated value reaches a value corresponding to a target value for the radiation dose as the reference value.

7. The apparatus according to claim 1, wherein the plurality of sensors are arrayed so as to form a plurality of rows and a plurality of columns,
the radiation imaging apparatus further includes a plurality of column signal lines corresponding to the plurality of columns,
each sensor of each column includes a detecting element configured to detect radiation and a transistor that connects the detecting element and the column signal line corresponding to the column, and
the drive unit is configured to drive the plurality of sensors row by row by setting each transistor corresponding to the sensor in an electrically conductive state.

8. The apparatus according to claim 7, wherein the control unit is further configured to perform the first control after the start of radiation irradiation by setting the transistor of each sensor arranged on some of the plurality of rows in an electrically conductive state at a predetermined cycle.

9. The apparatus according to claim 1, wherein the readout unit includes a differential amplifier, a first capacitor and a first switch element serially arranged on a first path that connects an output terminal of the differential amplifier and one input terminal, and a second capacitor and a second switch element serially arranged on a second path different from the first path and the second path connects the output terminal of the differential amplifier and the one input terminal, and
the control unit is further configured to change the operation mode of the readout unit by controlling the first switch element and the second switch element.

10. The apparatus according to claim 1, wherein the control unit is further configured to output a second control signal to start the radiation irradiation in response to a user pressing an exposure switch,
the control unit is further configured to read out by the readout unit signals from the some of the sensors as offset signals in a state in which the plurality of sensors are not irradiated with radiation, and
in the first control offset correction is performed by using the offset signals on the signals read out from the some of the sensors.

11. A radiation imaging system comprising:
the apparatus according to claim 1; and
the radiation source configured to irradiate radiation to the radiation imaging apparatus, wherein
the radiation source is configured to end the radiation irradiation to the radiation imaging apparatus based on the control signal.

12. A control method of a radiation imaging apparatus that includes a plurality of sensors arrayed on a substrate, a drive unit, a readout unit, and a control unit, comprising the steps of:
using said drive unit to drive said plurality of sensors by applying radiation irradiation from a radiation source thereto;
after radiation irradiation from said radiation source is started to the plurality of sensors, reading out by the readout unit signals from some of the plurality of sensors that have been driven by the driving unit in which signals are read out by changing an operation mode of the readout unit such that a value of an output of the readout unit is not saturated; and
outputting a control signal to end the radiation irradiation from the radiation source when a calculated value indicating a radiation dose based on an output of the readout unit in the reading out reaches a reference value in which the calculated value is calculated by accumulating the output of the readout unit in consideration of the signal amplification ratio of the readout unit, wherein
operation modes of the readout unit include a plurality of modes having different signal amplification ratios from each other.

13. A radiation imaging apparatus, comprising:
a plurality of sensors each configured to output a signal corresponding to radiation irradiation;
a drive unit configured to drive the plurality of sensors;
a readout unit configured to read out first signals from some of the plurality of sensors driven by the drive unit, and to read out second signals from the plurality of sensors driven by the drive unit, the second signals being different from the first signals;
a processor configured to generate image data based on the second signals; and
a control unit configured to perform (i) a first control to read out the first signals, by the readout unit, from the some of the plurality of sensors driven by the drive unit, (ii) a second control to calculate a value based on a monitor value obtained using the first signals, and to output a control signal to end the radiation irradiation when the calculated value reaches a reference value, and (iii) a third control to cause the processor to generate the image data based on the second signals which are read out, by the readout unit, from the plurality of sensors driven by the drive unit in response that the calculated value reached the reference value, wherein
the control unit is configured in the first control to change a signal amplification ratio of the readout unit during reading out the first signals by the readout unit, such that the monitor value is not saturated, and
the control unit is configured in the second control to calculate the calculated value, as a value which indicates a radiation dose, by accumulating the monitor value in consideration of the signal amplification ratio changed in the first control.

14. The apparatus according to claim 13, wherein the control unit is further configured to change the signal amplification ratio of the readout unit in the first control to be lower when the monitor value is larger than a first reference value, and to change the signal amplification ratio to be higher when the monitor value is smaller than a second reference value that is smaller than the first reference value.

15. The apparatus according to claim 14, wherein the control unit is further configured to change the signal amplification ratio in the first control to be higher when the monitor value is set to a steady state.

16. The apparatus according to claim 15, wherein the control unit is further configured to change the signal amplification ratio in the first control to be higher when a change amount of the monitor value becomes smaller than a predetermined amount.

17. The apparatus according to claim 13, wherein the control unit is further configured to output the control signal in the second control when the calculated value reaches a value corresponding to a target value for the radiation dose as the reference value.

18. The apparatus according to claim 13, wherein the plurality of sensors are arrayed so as to form a plurality of rows and a plurality of columns, the radiation imaging apparatus further includes a plurality of column signal lines corresponding to the plurality of columns, each sensor of each column includes a detecting element configured to detect radiation and a transistor that connects the detecting element and the column signal line corresponding to the column, and the drive unit is configured to drive the plurality of sensors row by row by setting each transistor corresponding to the sensor in an electrically conductive state.

19. The apparatus according to claim 18, wherein the control unit is further configured to perform the first control after the start of radiation irradiation by setting the transistor of each sensor arranged on some of the plurality of rows in an electrically conductive state at a predetermined cycle.

20. The apparatus according to claim 13, wherein the readout unit includes a differential amplifier, a first capacitor and a first switch element serially arranged on a first path that connects an output terminal of the differential amplifier and one input terminal, and a second capacitor and a second switch element serially arranged on a second path different from the first path and the second path connects the output terminal of the differential amplifier and the one input terminal, and the control unit is further configured to change the signal amplification ratio of the readout unit by controlling the first switch element and the second switch element.

21. The apparatus according to claim 13, wherein the control unit is further configured to output a second control signal to start the radiation irradiation in response to a user pressing an exposure switch, the control unit is further configured, after the exposure switch is pressed and before the second control signal is output, to read out by the readout unit signals from the some of the sensors as offset signals in a state in which the plurality of sensors are not irradiated with radiation, and in the first control offset correction is performed by using the offset signals on the signals read out from the some of the sensors.

22. A radiation imaging system comprising:

the apparatus according to claim 13; and the radiation source configured to irradiate the radiation to the radiation imaging apparatus, wherein the radiation source is configured to end the radiation irradiation to the radiation imaging apparatus based on the control signal.

23. A control method of a radiation imaging apparatus, the apparatus comprising a plurality of sensors each configured to output a signal corresponding to radiation irradiation, a drive unit configured to drive the plurality of sensors, a readout unit configured to read out first signals from some of the plurality of sensors driven by the drive unit and configured to read out second signals from the plurality of sensors driven by the drive unit, and a processor configured to generate image data based on the second signals, wherein the second signals are different than the first signals, the method comprising the steps of:

using the readout unit to read out the first signals from the some of the plurality of sensors driven by the drive unit;

calculating a value based on a monitor value obtained using the first signals, and outputting a control signal to end the radiation irradiation when the calculated value reaches a reference value; and causing the processor to generate the image data based on the second signals which are read out by the readout unit from the plurality of sensors driven by the drive unit in response that the calculated value reached the reference value, wherein a signal amplification ratio of the readout unit is changed while the readout unit reads out the first signals in the reading out the first signals, such that the monitor value is not saturated, and the calculated value is obtained as a value which indicates a radiation dose in the outputting the control signal by accumulating the monitor value in consideration of the signal amplification ratio changed in the reading out the first signals.

* * * * *